United States Patent [19]

Ishizumi et al.

[11] 4,263,304
[45] Apr. 21, 1981

[54] 7 H-INDOLO[2,3-C]ISOQUINOLINES

[75] Inventors: Kikuo Ishizumi; Junki Katsube, both of Toyonaka, Japan

[73] Assignee: Sumitomo Chemical Company, Limited, Osaka, Japan

[21] Appl. No.: 15,725

[22] Filed: Feb. 27, 1979

Related U.S. Application Data

[63] Continuation-in-part of Ser. No. 912,728, Jun. 5, 1978, abandoned.

[51] Int. Cl.³ .................. A61K 31/475; C01D 471/04
[52] U.S. Cl. ..................................... 424/262; 546/70; 544/125
[58] Field of Search .......................... 546/70; 424/262; 544/125

[56] References Cited

U.S. PATENT DOCUMENTS 4,014,883  3/1977  Fryer ........................... 260/288 CF Primary Examiner—Donald G. Daus
Assistant Examiner—D. B. Springer
Attorney, Agent, or Firm—Stevens, Davis, Miller & Mosher

[57] ABSTRACT

Novel indoloisoquinoline derivatives of the formula,

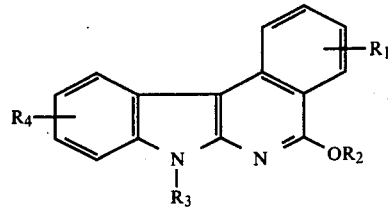

wherein $R_1$ and $R_4$ are each hydrogen, a halogen, nitro or $C_{1-4}$ alkoxy and $R_2$ and $R_3$ are each hydrogen, $C_{1-4}$ alkyl, $C_{2-4}$ alkenyl, a $C_{3-6}$ cycloalkyl-$C_{1-3}$ alkyl or a group of the formula,

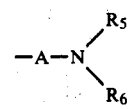

or -A-O-B wherein A is a $C_1$-$C_7$ alkylene; $R_5$ and $R_6$ are each hydrogen or $C_{1-4}$ alkyl, or, when taken together with the adjacent nitrogen atom, may form a 5- or 6-membered heterocyclic ring and B is hydrogen, $C_{1-4}$ alkyl, $C_{2-4}$ alkenyl or $C_{2-4}$ alkanoyl, provided that, when both $R_1$ and $R_4$ are hydrogen and $R_3$ is methyl, then $R_2$ can not be hydrogen, have potent anti-tumor activities.

5 Claims, No Drawings

7 H-INDOLO[2,3-C]ISOQUINOLINES

CROSS REFERENCE TO RELATED APPLICATION

This is a continuation-in-part of co-pending application Ser. No. 912,728 filed on June 5, 1978, now abandoned.

The present invention relates to indoloisoquinoline derivatives and preparation thereof.

More particularly, the invention pertains to 7H-indolo(2,3-c)isoquinoline derivatives having anti-tumor activities.

It was recently reported that the thermal reaction of 1-methyl-2-phenylcarbamoylamino-3-phenylindole(II) or 1-methyl-2-ethoxycarbonylamino-3-phenylindole(III) afforded 7-methyl-indolo(2,3-c)isoquinolin-5(6H)-one(IV) (Tetrahedron Letters, 1975, 3877).

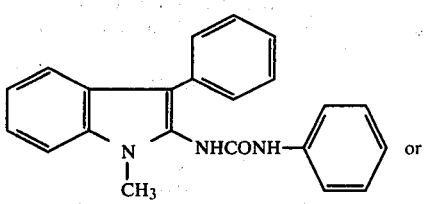

(II)

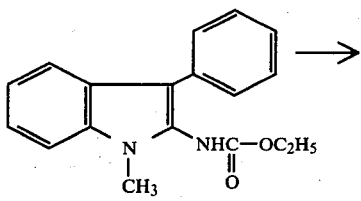

(III)

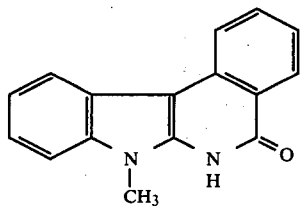

(IV)

Up to the present time, however, nothing has been known about the biological activities of the compound represented by the formula (IV).

The present inventors have now succeeded in the synthesis of a variety of novel indoloisoquinoline derivatives and have found that these compounds possess potent anti-tumor activities, and are useful for the treatment of tumors.

The compounds of the present invention are represented by the formula,

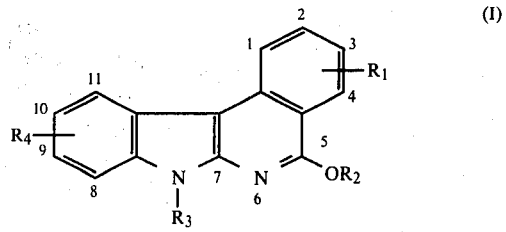

wherein $R_1$ and $R_4$ are each hydrogen, a halogen, nitro or a $C_{1-4}$ alkoxy; $R_2$ and $R_3$ are each hydrogen, a $C_{1-4}$ alkyl, a $C_2$–$C_4$ alkenyl, a $C_3$–$C_6$cycloalkyl-$C_1$–$C_3$alkyl or a group of the formula,

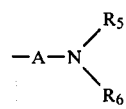

or —A—O—B (wherein A is straight or branched $C_{1-7}$ alkylene; $R_5$ and $R_6$ are each hydrogen or a $C_{1-4}$ alkyl, or when taken together with the adjacent nitrogen atom, may form a 5- or 6-membered heterocyclic ring; and B is hydrogen, a $C_{1-4}$ alkyl, a $C_{2-4}$ alkenyl or a $C_2$–$C_4$ alkanoyl), provided that said compound of the formula (IV) is excluded therefrom.

In the compounds of the formula (I) and elsewhere in the specification, the term "halogen" includes fluorine, chlorine, bromine and iodine; the term "$C_{1-4}$ alkyl" means straight or branched aliphatic hydrocarbons having 1 to 4 carbon atoms such as methyl, ethyl, propyl, isopropyl, butyl, isobutyl and so on; the term "$C_{1-4}$ alkoxy" means alkoxy groups having 1 to 4 carbon atoms such as methoxy, ethoxy, propoxy and so on; the term "$C_{3-6}$ cycloalkyl-$C_{1-3}$ alkyl" means such cycloalkylalkyl groups that have an alkyl having 1 to 3 carbon atoms, which is substituted with a cycloalkyl containing 3 to 6 carbon atoms, for example, cyclopropylmethyl, cyclobutylmethyl and so on; the term "straight or branched $C_{1-7}$ alkylene" includes, for example, methylene, ethylene, propylene, methyl-substituted propylene, butylene, dimethyl-substituted butylene, pentylene and so on; the term "$C_{2-4}$ alkanoyl" includes, for example, formyl, acetyl, propanoyl and so on; the term "$C_{2-4}$ alkenyl" means alkenyl groups having 2 to 4 carbon atoms such as allyl, butenyl and so on. Examples of the 5- or 6-membered heterocyclic ring represented by the formula

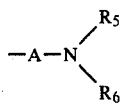

are pyrrolidino, piperidino, morpholino, 4-$C_{1-4}$ alkylpiperazino, 4-arylpiperazino (e.g., phenylpiperazino) and so on.

The compounds of the formula (I) wherein $R_2$ is hydrogen are tautomeric. Such tautomers are within the scope of the invention and are characterized by the formula,

[Structure (V): indoloisoquinoline with R₁, R₃, R₄, N-OH] ⇌ [Structure (V'): tautomer with N-H, C=O]

wherein R₁, R₃ and R₄ are as defined above.

Thus, an object of the present invention is to provide novel indoloisoquinoline derivatives of the formula (I), which are useful as anti-tumor agents.

Among the compounds of the general formula (I) of this invention, the compounds of the following formula (Ia) are preferable:

[Structure (Ia) with R₁, R₄, R₃', OR₂']

wherein R₁ and R₄ are as defined above, and both R'₂ and R'₃ are hydrogen, or either R'₂ or R'₃ is hydrogen and the other is a group of the formula $$-A-N\begin{matrix}R_5\\R_6\end{matrix}$$

(wherein A, R₅ and R₆ are as defined above).

Particularly preferred are the compounds of the formula (Ia) and R₅ and R₆ are independently methyl or ethyl, and A is ethylene or propylene.

Another object of the present invention is to provide effective and useful processes for the production of the compounds of the formula (I).

In the present invention, the compounds of the formula (I) can be prepared by reacting a compound of the formula,

[Structure (V)]

wherein R₁, R₃ and R₄ are as defined above, with a reactive ester derivative of a compound of the formula,

R₈—OH   (VIII)

wherein R₈ has the same meanings as R₂ except hydrogen atom, in the presence of a basic condensing agent.

As said reactive ester derivative of the alcohol of the formula (VIII), halides such as chlorides, bromides and iodides, and sulfonic esters such as arylsulfonic ester, benzenesulfonic ester, p-toluenesulfonic ester and methanesulfonic ester are preferably used.

Said basic condensing agent is exemplified by alkaline metal hydroxides, alkaline metal alkoxides, alkaline metal amides, alkaline metal hydrides, alkyl alkaline metals, and aryl alkaline metals.

Especially, such basic condensing agents as sodium methoxide, ethoxide, sodium hydroxide, potassium hydroxide, potassium carbonate, sodium amide, sodium hydride, butyl lithium, phenyllithium are suitablly used.

The reaction of the present invention may be effected at room temperature, but it may be accelerated by heating.

The reaction is preferably carried out in inert solvents. A variety of solvents can be mentioned as suitable solvents, such as water, alcohols such as methanol, ethanol, butanol and so on, aliphatic or aromatic hydrocarbons such as pentane, hexane, benzene, toluene and so on, ethers such as ethyl ether, tetrahydrofuran, dioxane, ethylene glycol dimethyl ether and so on, and aprotic polar solvents such as dimethylformamide or dimethylsulfoxide and so on.

Alternatively, the reaction of the present invention may be carried out by subjecting a reactive ester derivative of an alcohol of the formula (VIII) to condensation reaction with a basic metal salt of a compound of the formula (V).

The indoloisoquinolinones of the formula,

[Structure (V)]

wherein R₁, R₃ and R₄ are as defined above, can be prepared by heating an indole-2-isocyanate of the formula,

[Structure (VI)]

wherein R₁R₃ and R₄ are as defined above.

The reaction can be carried out by heating the compound of the formula (VI) at a temperature from 80 to about 260° C.

Alternatively, the reaction can also be conducted by heating a compound of the formula (VI) in the presence of a suitable inert organic solvent, preferably at refluxing temperature thereof. As a suitable inert solvent, those having a high boiling point may advantageously be used. They are, for example, dimethylformamide, ethylene glycol dimethyl ether, quinoline, xylene, anisol, chlorobenzene, nitrobenzene and so on.

The indole-2-isocyanates of the formula (VI) can be obtained by subjecting an indole-2-carboxazide of the formula,

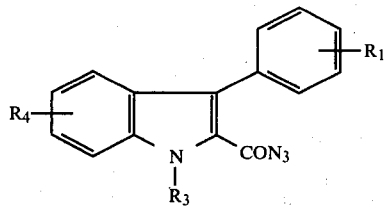

(VII)

wherein $R_1$, $R_3$ and $R_4$ are as defined above, to the Curtius rearrangement reaction in the presence or absence of a suitable solvent.

The reaction product of this Curtius rearrangement reaction, the compounds of the formula (VI), can be used for the preparation of the compounds of the formula (V) without isolation.

Compounds of the formula (Ia) may be taken out as pharmaceutically acceptable acid salts by the treatment with an acid, for example, a mineral acid such as hydrochloric acid, sulfuric acid, nitric acid and phosphoric acid, and an organic acid such as maleic acid, fumaric acid, succinic acid, citric acid, ethanesulfonic acid and ascorbic acid.

According to the process of the present invention, the following indoloisoquinoline derivatives, for example, can be obtained:

10-Chloro-7H-indolo(2,3-c)isoquinoline-5(6H)-one
10-Nitro-7H-indolo(2,3-c)isoquinoline-5(6H)-one
10-Methoxy-7H-indolo(2,3-c)isoquinolin-5-(6H)-one
1-Fluoro-10-chloro-7H-indolo(2,3-c)isoquinolin-5(6H)-one
7-Methyl-10-chloro-7H-indolo(2,3-c)isoquinolin-5(6H)-one
7-Methyl-10-nitro-7H-indolo-(2,3-c)isoquinolin-5(6H)-one
7-Cyclopropylmethyl-10-chloro-7H-indolo(2,3-c)-isoquinolin-5(6H)-one
7-β-Dimethylaminoethyl-10-chloro-7H-indolo(2,3-c)isoquinolin-5(6H)-one
5-Methoxy-7-methyl-10-chloro-7H-indolo-(2,3-c)isoquinoline
5-Cyclopropylmethyloxy-7methyl-10-chloro-7H-indolo-(2,3-c)isoquinoline
5-Allyloxy-7-methyl-10-chloro-7H-indolo(2,3-c)isoquinoline
5-Ethoxymethyloxy-7-methyl-10-chloro-7H-indolo(2,3-c)isoquinoline
5-β-Dimethylaminoethyloxy-7-methyl-10-chloro-7H-indolo(2,3-c)isoquinoline
5-β-Diethylaminoethyloxy-7-methyl-10chloro-7H-indolo(2,3-c)isoquinoline
5-γ-Dimethylaminopropyloxy-7methyl-10-chloro-7H-indolo(2,3-c)isoquinoline
5-γ-Dimethylaminobutyloxy-7-methyl-10-chloro-7H-indolo(2,3-c)isoquinoline
5-β-Morpholinoethyloxy-7-methyl-10chloro-7H-indolo(2,3-c)isoquinoline
5-β-Hydroxyethyloxy-7-methyl-10-chloro-7H-indolo(2,3-c)isoquinoline
5-β-Dimethylaminoethyloxy-7-cyclopropylmethyl-10chloro-7H-indolo(2,3-c)isoquinoline The compounds of formula I and their pharmaceutically acceptable salts are useful as antitumor agents. Thus, they inhibit the growth of transplantable tumors, for example, Sarcoma 180 (S-180), in mice. The useful inhibitory activity of the compounds of formula I against transplantable tumors can be demonstrated in warm-blooded animals. For example, mice are weighed and divided into groups of six animals for each drug and control group. $3 \times 10^8$ Cells of S-180 tumor are injected im in hinder leg. Mice are treated i.p. with 200 mg/kg dose and then once on every second day until five treatments are given. The mice are sacrificed ten days after implantation. The weight of each excised tumor is determined and averaged for each group of six mice. The difference between the average tumor weight of the untreated controls (C) and the average tumor weight of each treated group (T) is divided by C. The results are expressed as (C-T)/C (%).

When 5-β-dimethylaminoethoxy-7-methyl-10-chloro-7H-indolo[2,3-c]isoquinoline is used as the test substance, the result is 81.6% at 200 mg/kg i.p., administered once on every second day for 10 days.

1-Fluoro-10-chloro-7H-indolo[2,3-c]isoquinolin-5(6H)-one gives the result of 73.0% inhibition of the growth of the tumor at same dosage as above.

The dosage of the active agents will vary with the form of administration and the particular compound chosen. Furthermore, it will vary with the particular host under treatment. Generally, treatment is intiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is a range of from about 10 to 500 mg per kilogram of body weight of warm-blood animals although as aforementioned variations will occur.

The compounds of formula I can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene glycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The present invention will be illustrated more concretely with reference to the following examples, which are given by way of illustration and not by way of limitation of the present invention.

EXAMPLE 1

2-Isocyanato-3-(o-fluorophenyl)-5-chloro indole (2.0 g) is heated at 240-260° C. in an oil bath for 20 minutes. After cooling, the resulting solid is washed with ethanol and collected by filtration. Recrystallization of the thus obtained crystals from dimethylforamide gives 0.92 g of 1-fluoro-10-chloro-7H-indolo(2,3-c)isoquinolin-5(6H)-one, melting point > 300° C.

EXAMPLE 2

3-Phenyl-5-chloroindole-2-carboxazide (1.32 g) is heated gradually up to 240-260° C. and at this temperature for 20 minutes. After cooling, the resulting solid is washed with ethanol and collected by filtration. Recrystallization of the thus obtained crystals from dimethylformamide gives 0.96 g of 10-chloro-7H-indolo-(2,3-c)isoquinolin-5(6H)-one, melting point > 300° C.

3-Phenyl-5-chloroindole-2-carboxazide is prepared as follows:

3-Phenyl-5-chloroindole-2-carboxylic acid (13.48 g) is added to thionyl chloride (47 g) and the mixture is refluxed for 1 hour. After removal of excess thionyl chloride under reduced pressure, acetone (120 ml) is added to the residue. To this, cooled to −1° C., sodium azide (4.85 g) in water (15 ml) is added in one portion with stirring. The reaction mixture is stirred for further 40 minutes at 5°–10° C., and 120 ml of water is added thereto. Separation of precipitates by filtration gives 16.49 g of 3-phenyl-5-chloroindole-2-carboxazide (melting point 133° C. (decomp.)).

EXAMPLE 3

1-Methyl-2-isocyanato-3-phenyl-5-nitroindole (3,27 g) is heated at 240°–250° C. in an oil bath for 3 hours. The resulting crystals are washed with ethanol and collected by filtration to give 3.25 g of 7-methyl-10-nitro-7H-indolo(2,3-c)isoquinolin-5(6H)-one, melting point > 300° C.

1-Methyl-2-isocyanato-3-phenyl-5-nitroindole is prepared as follows:

1-Methyl-3-phenyl-5-nitroindiole-2-carboxazide [melting point 102°–106° C. (decomp.)] (300 mg) is heated at 60° C. for 8 hours under reduced pressure to give 230 mg of 1-methyl-2-isocyanato-3-phenyl-5-nitroindole, melting point > 250° C.

EXAMPLE 4

1-Methyl-2-isocyanato-3-phenyl-5-chloroindole (3.0 g) is heated at 100°–120° C. in an oil bath for 4 hours. Dimethylformamide (10 ml) is added to the reaction mixture and then refluxed for 30 minutes. After cooling, precipitates are separated by filtration and washed with ethanol to give 2.5 g of 7-methyl-10-chloro-7H-indolo(2,3-c)isoquinolin-5(6H)-one, melting point > 300° C.

1-Methyl-3-phenyl-5-chloroindole-2-carboxazide [melting point 91°–94° C. (decomp)] is heated at 60° C. for 10 hours under reduced pressure to give 1-methyl-2-isocyanato-3-phenyl-5-chloroindole [melting point 150° C. (decom.)] quantitatively.

EXAMPLE 5

1-Methyl-2-isocyanato-3-phenyl-5-chloroindole (3.0 g) in 10 ml of dimethylformamide is heated with stirring at reflux temperature for 1 hour. After cooling, precipitates are separated by filtration to give 2.5 g of 7-methyl-10-chloro-7H-indolo(2,3-c)isoquinolin-5(6H)-one, melting point > 300° C.

EXAMPLE 6

1-Methyl-3-phenyl-5-chloroindole-2-carboxazide (1.0 g) in 3 ml of dimethylformamide is heated with stirring at reflux temperature for 2 hours. After cooling, precipitates are separated by filtration to give 0.76 g of 7-methyl-10-chloro-7H-indolo(2,3-c)isoquinoline-5(6H)-one, melting point > 300° C.

EXAMPLE 7

1-Cyclopropylmethyl-2-isocyanato-3-phehyl-5-chloroindole (0.5 g) is heated at 100°–120° C. in an oil bath for 4 hours. After cooling, the resulting crystals are washed with ethanol and collected by filtration to give 7-cyclopropylmethyl-10-chloro-7H-indolo(2,3-c)isoquinolin-5(6H)-one, melting point > 300° C.

EXAMPLE 8

To a stirred suspension of 0.08 g of 65% sodium hydride (in oil) in 5 ml of dimethylformamide, 0.5 g of 7-methyl-10-chloroindolo(2,3-c)isoquinolin-5(6H)-one is added at room temperature. The reaction mixture is stirred for 30 minutes and 2.5 g of methyl iodide in 30 ml of dimethylformamide is added dropwise thereto at room temperature. After addition, stirring is continued for further 16 hours at room temperature and then dimethylformamide is removed under reduced pressure. The residue is treated with water and extracted with dichloromethane. The organic layer is dried over magnesium sulfate and the solvent is evaporated in vacuo to give 404 mg of 5-methoxy-7-methyl-10-chloro-7H-indolo(2,3-c)isoquinoline, which is recrystallized from ethyl acetate, melting point 179°–180.5° C.

EXAMPLE 9

5-Ethoxy-7-methyl-10-chloro-7H-indolo(2,3-c)isoquinoline (melting point 161°–163° C.) is prepared from 7-methyl-10-chloro-7H-indolo(2,3-c)isoquinolin-5(6H)-one, sodium hydride and ethyl bromide by the method described in Example 8.

EXAMPLE 10

5-Cyclopropylmethyloxy-7-methyl-10-chloro-7H-indolo(2,3-c)isoquinoline (melting point 141°–142° C.) is prepared from 7-methyl-10-chloro-7H-indolo(2,3-c)isoquinolin-5(6H)-one, sodium hydride and cyclopropylmethyl bromide by the method described in Example 8.

EXAMPLE 11

5-β-Ethoxyethyloxy-7-methyl-10-chloro-7H-indolo(2,3-c)isoquinoline (melting point 93.5°–95.5° C.) is prepared from 7-methyl-10-chloro-7H-indolo(2,3-c)isoquinolin-5(6H)-one, sodium hydride and β-ethoxyethyl bromide by the method described in Example 8.

EXAMPLE 12

5-Allyloxy-7-methyl-10-chloro-7H-indolo(2,3-c)isoquinoline (melting point 147°–148° C.) is prepared from 7-methoxy-10-chloro-7H-indolo(2,3-c)isoquinolin-5(6H)-one, sodium hydride and allyl chloride by the method described in Example 8.

EXAMPLE 13

5-Vinyloxy-7-methyl-10-chloro-7H-indolo(2,3-c)isoquinoline (melting point 121°–124° C.) is prepared from 7-methyl-10-chloro-7H-indolo(2,3-c)isoquinolin-5(6H)-one, sodium hydride and vinyl bromide by the method described in Example 8.

EXAMPLE 14

5-β-Morpholinoethyloxy-7-methyl-10-chloro-7H-indolo(2,3-c)isoquinoline (melting point 140°–142° C.) is prepared from 7-methyl-10-chloro-7H-indolo(2,3-c)isoquinolin-5(6H)-one, sodium hydride and β-morpholinoethyl chloride by the method described in Example 8.

EXAMPLE 15

5-β-Dimethylaminoethyloxy-7-methyl-10-chloro-7H-indolo(2,3-c)isoquinoline (melting point 98°–99.5° C.) is prepared from 7-methyl-10-chloro-7H-indolo(2,3-c)isoquinolin-5(6H)-one, sodium hydride and β-dimethylaminoethyl chloride by the method described in Example 8.

EXAMPLE 16

5-β-Diethylaminoethyloxy-7-methyl-10chloro-7H-indolo(2,3-c)isoquinoline (hydrochloride melting point 236°–237° C.) is prepared from 7-methyl-10-chloro-7H-indolo(2,3-c)isoquinolin-5(6H)-one, sodium hydride and β-diethylaminoethyl chloride by the method described in Example 8.

EXAMPLE 17

5-β-Dimethylaminoethyloxy-7-cyclopropylmethyl-10-chloro-7H-indolo(2,3-c)isoquinoline (melting point 155°–157° C.) is prepared from 7-cyclopropylmethyl-10-chloro-7H-indolo(2,3-c)isoquinolin-5(6H)-one, sodium hydride and β-dimethylaminoethyl chloride by the method described in Example 8.

What is claimed is:

1. A compound of the formula

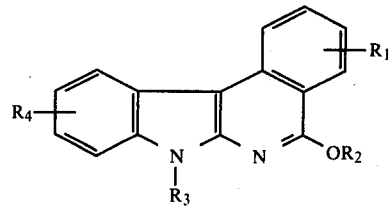

wherein $R_1$ and $R_4$ are each hydrogen, halogen, nitro or $C_{1-4}$ alkoxy; $R_2$ and $R_3$ are each hydrogen, $C_{1-4}$ alkyl, $C_{2-4}$ alkenyl, $C_{3-6}$-cycloalkyl-$C_{1-3}$alkyl or a group of the formula

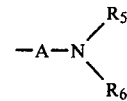

or —A—O—B wherein A is a straight or branched $C_{1-7}$ alkylene; $R_5$ and $R_6$ are each hydrogen, or $C_{1-4}$ alkyl; B is hydrogen, $C_{1-4}$ alkyl, $C_{2-4}$ alkenyl or $C_{2-4}$ alkanoyl, provided that, when both $R_1$ and $R_4$ are hydrogen and $R_3$ is methyl, $R_2$ can not be hydrogen, and their pharmaceutically acceptable acid addition salts.

2. A compound according to claim 1, wherein both $R_2$ and $R_3$ are hydrogen or either $R_2$ or $R_3$ is hydrogen and the other is a group of the formula

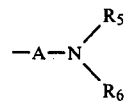

wherein A, $R_5$ and $R_6$ are as defined in claim 1.

3. A compound according to claim 2, wherein $R_5$ and $R_6$ are each methyl or ethyl and A is ethylene or propylene.

4. A compound according to claim 3, wherein $R_5$ and $R_6$ are methyl and A is ethylene.

5. A composition useful for the treatment of transplantable tumors in warm-blood animals which comprises as an active ingredient a compound of claim 1 or its salt.

* * * * *